（12）United States Patent
Alayil et al.

(10) Patent No.: US 12,287,107 B2
(45) Date of Patent: Apr. 29, 2025

(54) INDOOR AIR QUALITY MONITORS FOR HVAC SYSTEMS

(71) Applicant: Lennox Industries Inc., Richardson, TX (US)

(72) Inventors: Rajesh Alayil, Kerala (IN); Henry Todd Greist, Gainesville, FL (US); Sanjeev Hingorani, Gainesville, FL (US); Thomas John Wolowicz, Allen, TX (US)

(73) Assignee: Lennox Industries Inc., Richardson, TX (US)

( * ) Notice: Subject to any disclaimer, the term of this patent is extended or adjusted under 35 U.S.C. 154(b) by 378 days.

(21) Appl. No.: 17/829,171

(22) Filed: May 31, 2022

(65) Prior Publication Data

US 2023/0383981 A1 Nov. 30, 2023

(51) Int. Cl.

| | |
|---|---|
| *F24F 11/89* | (2018.01) |
| *F24F 11/30* | (2018.01) |
| *F24F 11/74* | (2018.01) |
| *G01N 15/06* | (2024.01) |
| *F24F 13/20* | (2006.01) |
| *F24F 110/64* | (2018.01) |
| *F24F 110/70* | (2018.01) |
| *G01N 33/00* | (2006.01) |

(52) U.S. Cl.
CPC .............. *F24F 11/74* (2018.01); *F24F 11/30* (2018.01); *F24F 11/89* (2018.01); *G01N 15/06* (2013.01); *F24F 13/20* (2013.01); *F24F 2110/64* (2018.01); *F24F 2110/70* (2018.01); *G01N 33/004* (2013.01)

(58) Field of Classification Search
None
See application file for complete search history.

(56) References Cited

U.S. PATENT DOCUMENTS

| | | | | |
|---|---|---|---|---|
| 4,758,827 A | * | 7/1988 | Powers ................ | G08B 17/113 116/273 |
| 5,844,148 A | * | 12/1998 | Klein .................... | G01N 1/2226 73/864.81 |
| 12,117,188 B2 | * | 10/2024 | Alayil ....................... | F24F 3/16 |
| 2006/0099904 A1 | * | 5/2006 | Belt .................... | G05D 23/1932 454/236 |
| 2013/0160571 A1 | * | 6/2013 | Williamson ......... | G01N 1/2247 138/108 |

* cited by examiner

*Primary Examiner* — Jerry-Daryl Fletcher
*Assistant Examiner* — Daniel C Comings
(74) *Attorney, Agent, or Firm* — Johnston IP Law, PLLC

(57) ABSTRACT

A heating, ventilating, and air conditioning (HVAC) system includes at least one indoor air quality monitor. The indoor air quality monitor is formed with an arrangement of chambers—intake chamber, low-flow chamber, and outlet chamber—such that a particulate sensor on an interior and another air quality sensor are neither overwhelmed nor underwhelmed by air flow to the sensors. The indoor air quality monitor may be arranged for attaching to a surface in a conditioned space for sampling air therein or may include a bypass chamber that fluidly couples to an HVAC duct.

18 Claims, 9 Drawing Sheets

INDOOR AIR QUALITY MONITORS FOR HVAC SYSTEMS

TECHNICAL FIELD

This is directed, in general, to heating, ventilating and air conditioning or cooling (HVAC) systems, and more specifically to indoor air quality monitors for HVAC Systems.

BACKGROUND

The following discussion of the background is intended to facilitate an understanding of the present disclosure only. It should be appreciated that the discussion is not an acknowledgment or admission that any of the material referred to was part of the common general knowledge at the priority date of the application.

Heating, ventilating, and air conditioning (HVAC) systems can be used to regulate the environment within an enclosed space. Typically, an air blower is used to pull air (i.e., return air) from the enclosed space into the HVAC system through ducts and push the air into the enclosed space through additional ducts after conditioning the air (e.g., heating or cooling). Unless otherwise indicated, as used throughout this document, "or" does not require mutual exclusivity. Various types of HVAC systems may be used to provide conditioned air for enclosed spaces. At times it is desirable to monitor the air quality associated with an HVAC system.

SUMMARY

According to an illustrative embodiment, an indoor air quality monitor for a heating, ventilating, and air conditioning (HVAC) system includes a first cover having a first sidewall, a second sidewall, a primary wall, a third sidewall, and a fourth sidewall. The first cover has a first concave interior portion. The system further includes a plurality of chamber walls extending from the primary wall of the first cover into the first concave interior portion. One of the chamber walls of the plurality of chamber walls is a longitudinal partitioning wall extending from the primary wall into the first concave interior portion. The longitudinal partitioning wall has a first surface and a second surface and has a first aperture and a second aperture. The system includes a particulate sensor disposed on the first surface of the longitudinal partitioning wall with a sensor intake aligned with the first aperture through the longitudinal partitioning wall and a sensor outlet aligned with the second aperture through the longitudinal partitioning wall. The system further includes a second cover having a first sidewall, a second sidewall, a primary wall, a third sidewall, and a fourth sidewall. The second cover has a second concave interior portion.

The first cover and second cover mate and couple with the first concave interior portion and the second concave interior portion facing each other and forming an interior cavity when in an assembled position. The system also includes a wall gasket disposed on a portion of the second cover in the second concave interior portion. When assembled, the plurality of chamber walls interfaces at least partially with the wall gasket and forms at least three chambers: an intake chamber, a low-flow chamber, and an outlet chamber. The first aperture of the longitudinal partitioning wall is fluidly coupled to the intake chamber and the second aperture of the longitudinal partitioning wall is fluidly coupled to a portion of the outlet chamber. At least one wall of the plurality of chamber walls that forms the intake chamber includes a cutout to fluidly couple the intake chamber and the low-flow chamber.

The fourth sidewall of the second cover is formed with a first aperture and a second aperture for providing fluid access to the intake chamber and outlet chamber, respectively. The system also has a bypass chamber having an intake conduit and an outlet conduit and having a tributary outlet and a tributary inlet. When assembled, the tributary outlet is fluidly coupled to the intake chamber and the tributary inlet is fluidly coupled to the outlet chamber. At least one air quality sensor disposed in the low-flow chamber.

According to another illustrative embodiment, an HVAC system includes a blower, a control unit communicatively coupled to the blower for controlling operation of the blower, and an indoor air quality monitor communicatively coupled to the control unit for providing air quality data thereto. The controller is responsive in activating or deactivating the blower in response to the air quality data.

The indoor air quality monitor includes a monitor body having an interior cavity and a plurality of chambers formed within the interior cavity. One of the plurality of chambers within the interior cavity is an intake chamber. The intake chamber is fluidly coupled to a first aperture in the monitor body. Another of the plurality of chambers within the interior cavity is an outlet chamber. The outlet chamber is fluidly coupled to a second aperture in the monitor body. Another of the plurality of chambers within the interior cavity is a low-flow chamber that is fluidly coupled to the intake chamber. The indoor air quality monitor also has a particulate sensor fluidly coupled to the intake chamber. The particulate sensor includes a fan for pulling air from the intake chamber. The indoor air quality monitor also includes a $CO_2$ sensor fluidly disposed within the low-flow chamber.

According to still another illustrative embodiment, a method of monitoring air quality in an HVAC system includes fluidly coupling an offtake conduit to a duct of the HVAC system and to an inlet conduit of a bypass chamber of an indoor air quality of monitor and fluidly coupling a return conduit to the duct and to an outlet conduit of the bypass chamber. The method further includes coupling the bypass chamber to a monitor body of an indoor air quality monitor and siphoning air from the bypass chamber into an interior of the monitor body of the indoor air quality monitor, which comprises a particulate sensor and a $CO_2$ sensor. The $CO_2$ sensor is in a low-flow chamber in the interior of the monitor body and the particulate sensor includes a fan that pulls air from an intake chamber and discharges the air to an outlet chamber. The method also includes returning air from the outlet chamber to the bypass chamber and returning air through the return conduit from the bypass chamber to the duct.

DESCRIPTION OF THE DRAWINGS

Illustrative embodiments of the present invention are described in detail below with reference to the attached drawing figures, which are incorporated by reference herein and wherein.

DETAILED DESCRIPTION

In the following detailed description of the preferred embodiments, reference is made to the accompanying drawings that form a part hereof, and in which is shown, by way of illustration, specific embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the invention, the description may omit certain information known to those skilled in the art. The following detailed description is, therefore, not to be taken in a limiting sense, and the scope of the present invention is defined only by the claims.

Unless otherwise indicated, as used throughout this document, "or" does not require mutual exclusivity.

Figure 1:
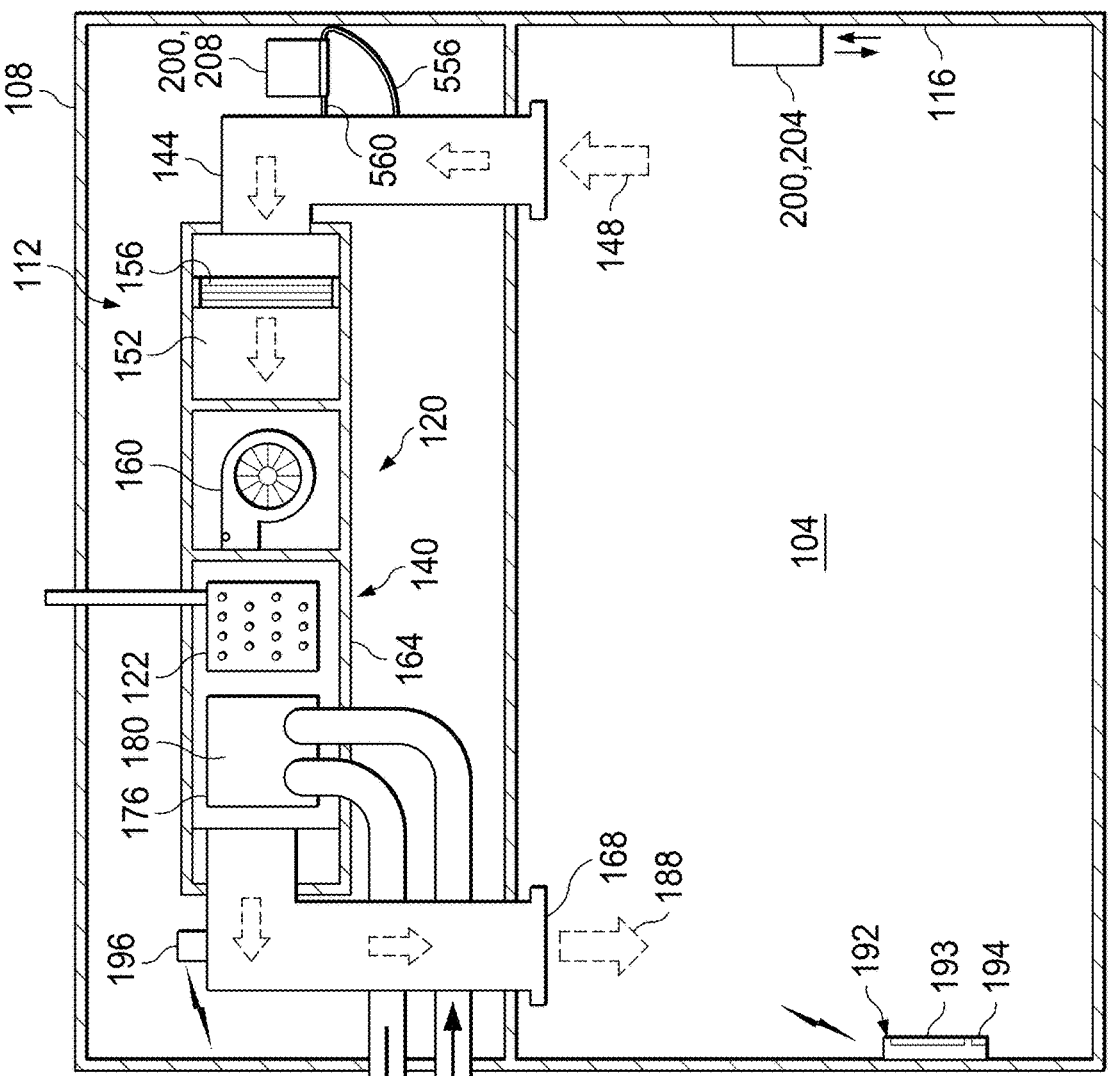
FIG. 1 is a schematic diagram of a heating, ventilating, and air conditioning system having an indoor air quality monitor according to one illustrative embodiment.
Figure 1:
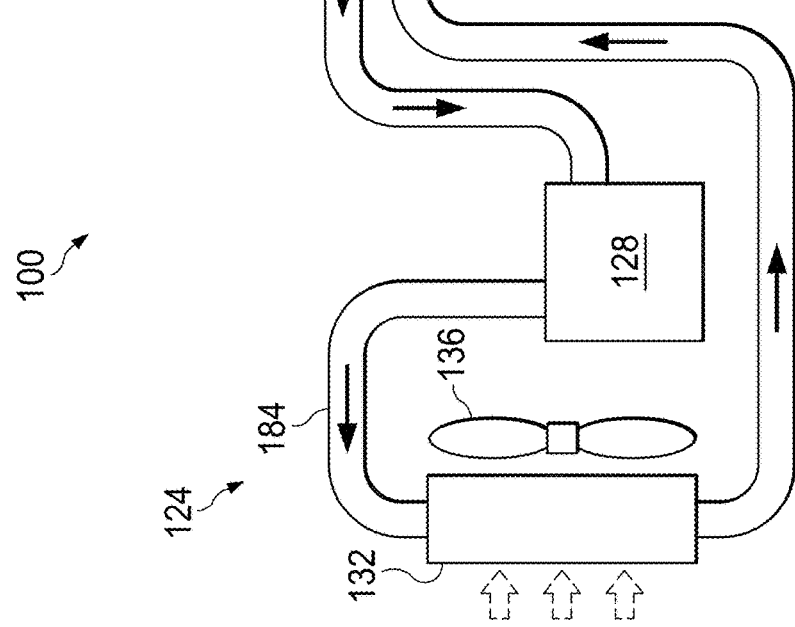

Referring now to the drawings and initially to FIG. 1, a heating, ventilating, and air conditioning (HVAC) system 100 is presented. The HVAC system 100 is for providing conditioned air to a first closed space or conditioned space 104 such as the interior of a building or house 108. At least a portion of the HVAC system 100 is disposed within a second closed space 112, or equipment space, e.g., an attic or air handler closet. The spaces may be defined by a plurality of walls 116. In this embodiment, a portion 120 of the system 100 is located within the building, i.e., within the second closed space 112, and a portion 124 outside the building. Typically, at least the compressor 128, a condenser coil 132, and a fan 136 are located outside. In a heat pump mode, the condenser and evaporator are switched using a reversing valve.

The HVAC system 100 includes an HVAC unit 140 that is disposed within the second closed space 112, or equipment space. The HVAC unit 140 includes a return air duct 144 that receives intake air 148 from the first closed space 104. The return air duct 144 may include or be coupled to a transition duct 152 that may include one or more filters 156. A blower 160 pulls the return air into the return air duct 144. The blower 160 is fluidly coupled to the return air duct 144. The blower 160 moves air into a conditioning compartment 164.

The conditioning compartment or unit 164 is fluidly coupled to the blower 160 for receiving air therefrom to be treated. The conditioning compartment 164 is formed with a plurality of chamber walls. The conditioning compartment 164 may include a portion of a delivery duct in some embodiments.

The conditioning compartment 164 includes a heating device 122 and a cooling unit 176. The cooling unit 176 includes an evaporator 180 fluidly coupled to the closed-conduit circuit 184.

The conditioning compartment 164 produces a treated or conditioned air 188 that is delivered into the first closed space 104 by the delivery duct 168. The delivery duct 168 is fluidly coupled to the conditioning compartment 164 for discharging the treated air 188 from the conditioning compartment 164 into the first closed space 104.

The HVAC system 100 may include one or more controllers. For example, the controller can be a smart thermostat 192 in the first closed space, or conditioned space, 104 or another controller 196 elsewhere. The controllers 192, 196 may include one or more processors and one or more non-transitory memories, e.g., 193, 194.

The one or more processors of the controllers and the one or more processors may be configured to execute one or more sequences of instructions, programming or code stored on or in the one or more non-transitory memories, which includes all types of memory devices and includes readable medium used for storage. The processor can be, for example, a general-purpose microprocessor, a microcontroller, a digital signal processor, an application specific integrated circuit, a field programmable gate array, a programmable logic device, a controller, a state machine, a gated logic, discrete hardware components, an artificial neural network or any like suitable entity that can perform calculations or other manipulations of data. The memory, e.g., memory 193, may include one or more the following: random access memory (RAM), flash memory, read only memory (ROM), programmable read only memory (PROM), erasable PROM, registers, hard disks, removable disks, CD-ROMS, DVDs, or any other suitable storage devices.

The HVAC system 100 may also include one or more indoor air quality monitors 200, such as a wall-mounted indoor air quality monitor 204 or a duct-sampling indoor air quality monitor 208. The duct-sampling indoor air quality monitor 208 may be positioned to sample unfiltered, unhumidified, un-ventilated air in the duct 144. Illustrative embodiments of the indoor air quality monitors 200 are described further below.

The smart thermostat 192 may be disposed within the first closed space 104. The thermostat 192 may provide control signals to the blower 160, heating device 172, or cooling unit 176 (or cooling subsystem) in response to a temperature in the first closed space 104. The thermostat 192 or controller 196 may be communicatively coupled to the one or more indoor air quality monitors 200 and respond thereto. For example, if the air quality is bellowed a threshold, the thermostat 192/controller 196 may activate or increase the blower 160 or if the air quality is higher than needed, the blower 160 may be deactivated or slowed. Aspects of the operation of the HVAC system 100 may be modified in response to the air quality data developed by the indoor air quality monitors 200.

The thermostat/control unit 192 may include an input device and a display, such as a touch-screen display and a speaker for audible alerts or instructions. In some embodiments, the control unit 192 is communicatively coupled, e.g., by wireless signal or wired signal, to a processing unit or controller 196. In some embodiments, the control unit 192 and the processing unit 196 may be the same unit.

Figure 2:
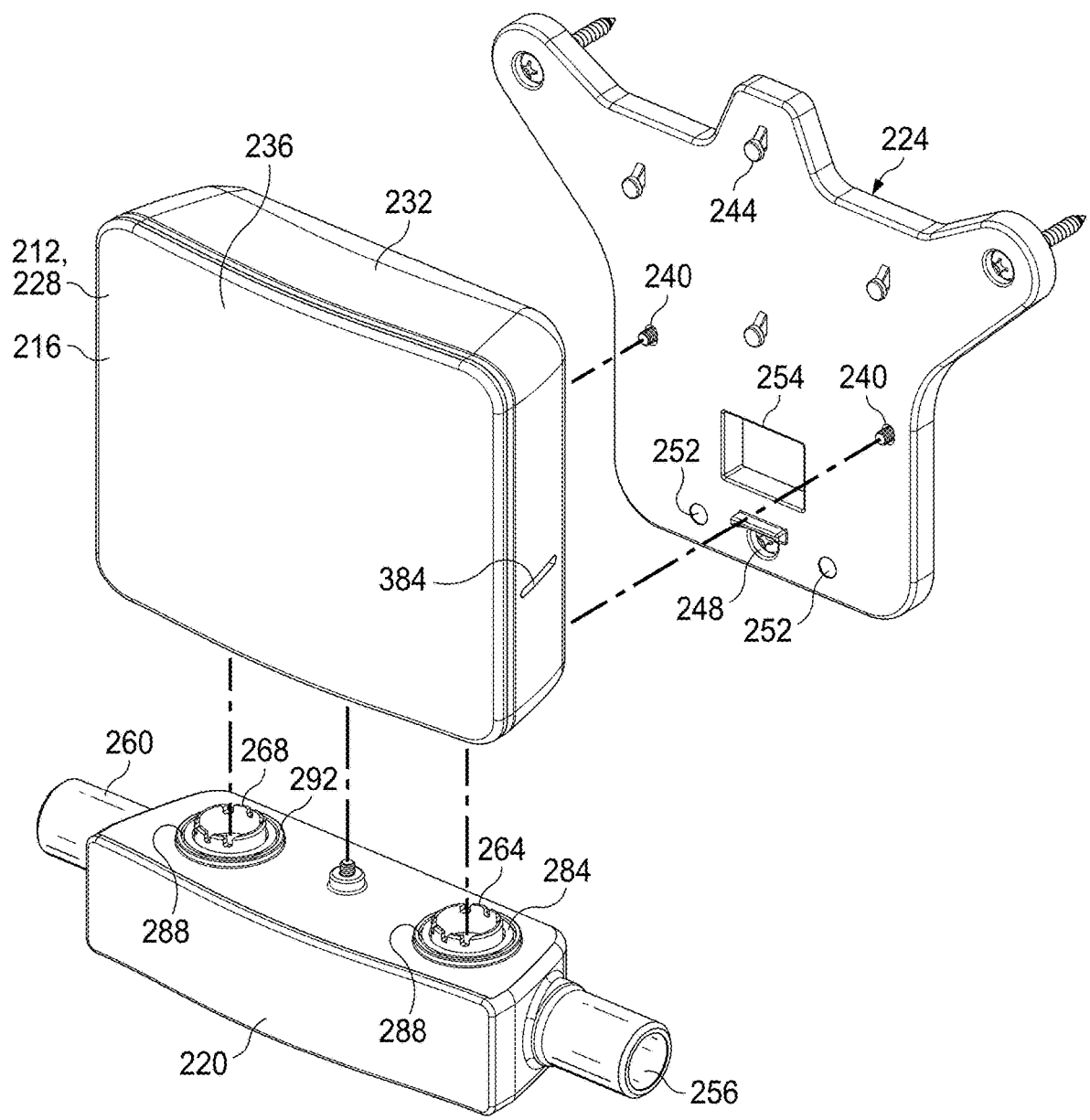
FIG. 2 is a schematic, partially exploded, perspective view of an illustrative embodiment of an indoor air quality monitor.

Referring now primarily to FIG. 2, an indoor air quality monitor 212 for a heating, ventilating, and air conditioning system, e.g., the system 100 of FIG. 1, is presented. In one illustrative embodiment, the three major components shown, a sensing unit 216, bypass chamber 220, and a mounting bracket 223 may be presented to a customer assembled and may be disassembled as desired for different applications. For clarity, the sensing unit 216, the bypass chamber 220, and the mounting bracket 224 are shown separated. All three may be formed from any suitable material, e.g., a thermoplastic polymer. In some embodiment, the sensing unit 216 may be mounted in an indoor, conditioned space, e.g., space 104 in FIG. 1, without a bypass chamber 220 or may be mounted near a duct 144 as also shown in FIG. 1. When mounting for the duct application, the bypass chamber 220 is required, but the bypass chamber 220 is not required for a conditioned-space application.

The sensor unit 216 of the indoor air quality monitor 212 may comprises a monitor body 228. In one illustrative embodiment, the monitor body 228 may comprise a first cover 232 and a second cover 236 that are coupled to form an interior cavity therebetween.

The mounting bracket 224 may be attached to a wall or equipment surface using fastener apertures 240 and fasteners (not explicitly shown), such as screws or bolts. Mounting pins 244 may be inserted into keyways 532 (FIG. 8) on the primary wall of the second cover. If the bypass chamber 220 is to be included, the mounting shelf 248 and fastener apertures 252 may be used. The mounting shelf 248 interfaces with a mounting hood or shelf (552 in FIG. 9) on an exterior of the bypass chamber 220. The mounting bracket 224 includes bracket cutout 254. A mounting hood or shelf 552 (FIG. 9) on the bypass chamber 220 tucks through the rectangular opening or cutout 254 and the vertical features of hood 552 fit inside the cutout 254 to stabilize it from rotation and to support the downward pressure or better seal between the sensor and the bypass chamber 220.

The bypass chamber 220 is formed with an intake conduit 256 and an outlet conduit 260. The bypass chamber 220 includes a tributary outlet 264 and a tributary inlet 268. The bypass chamber 220 may further include a first ring extension or protrusion 272 extending around the tributary outlet 264 and second ring extension or protrusion 276 extending around the tributary inlet 268. A first seal groove 280 may be formed about the first ring extension 264 for receiving a first O-ring 284. Likewise, a second seal groove 288 may be formed about the second ring extension 276 and have a second O-ring 292. A screw boss 293 with a fastener 294, e.g., a screw or bolt, is shown.

Figure 3:
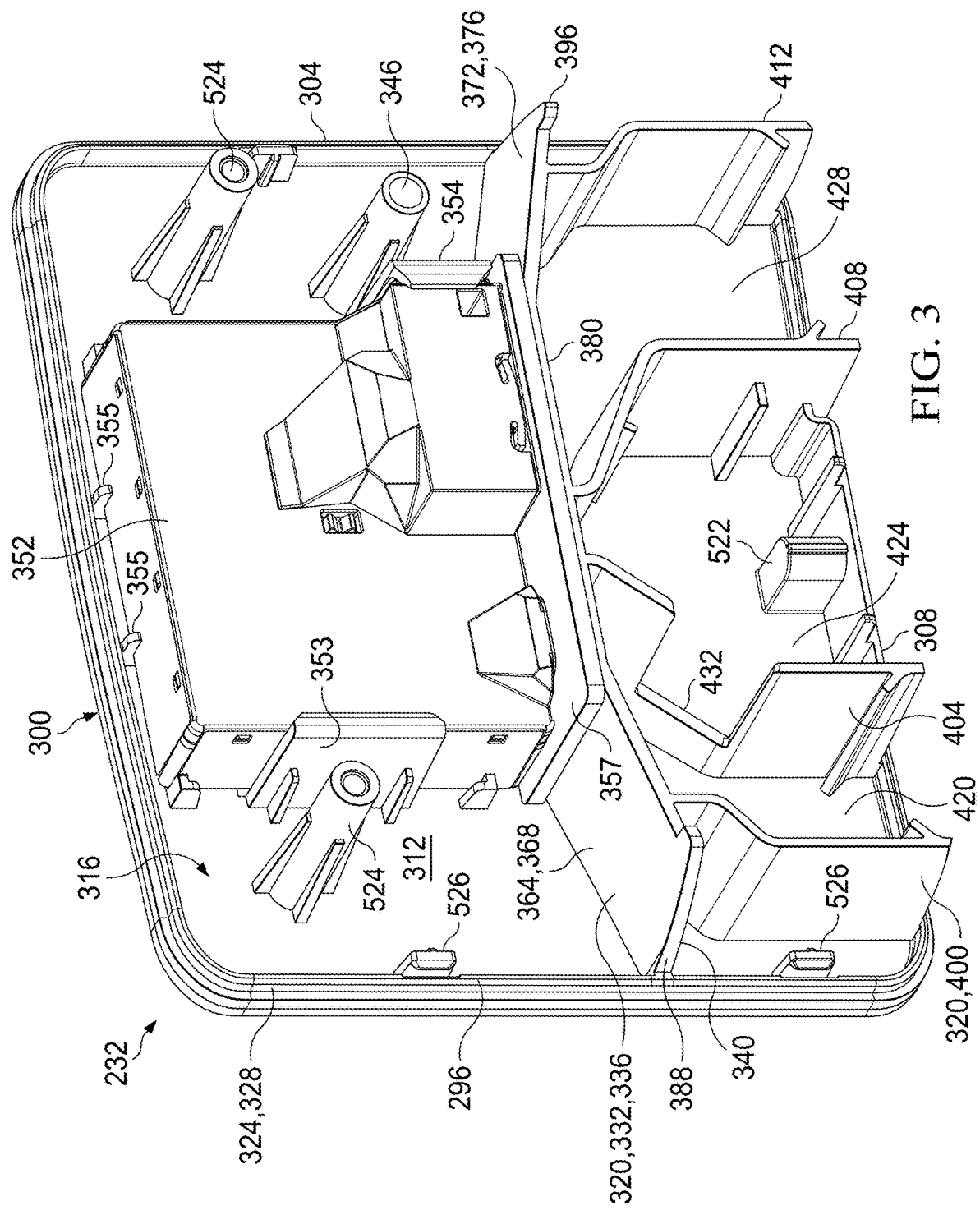
FIG. 3 is a schematic, perspective view of a first cover of an illustrative embodiment of an indoor air quality monitor.
Figure 4:
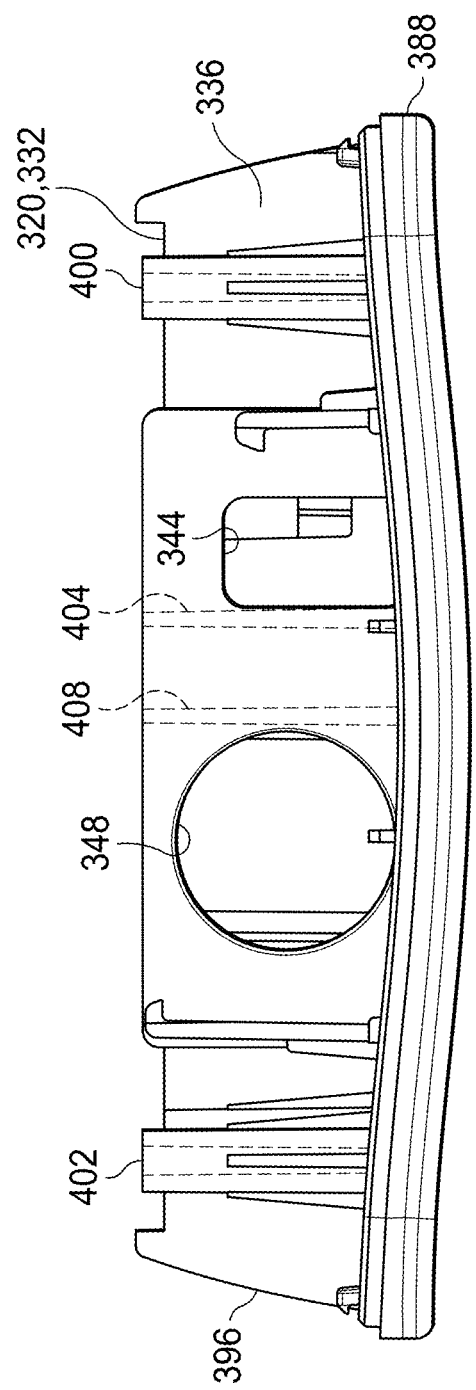
FIG. 4 is a schematic top view of a longitudinal partitioning wall of an illustrative embodiment of an indoor air quality monitor.
Figure 5:
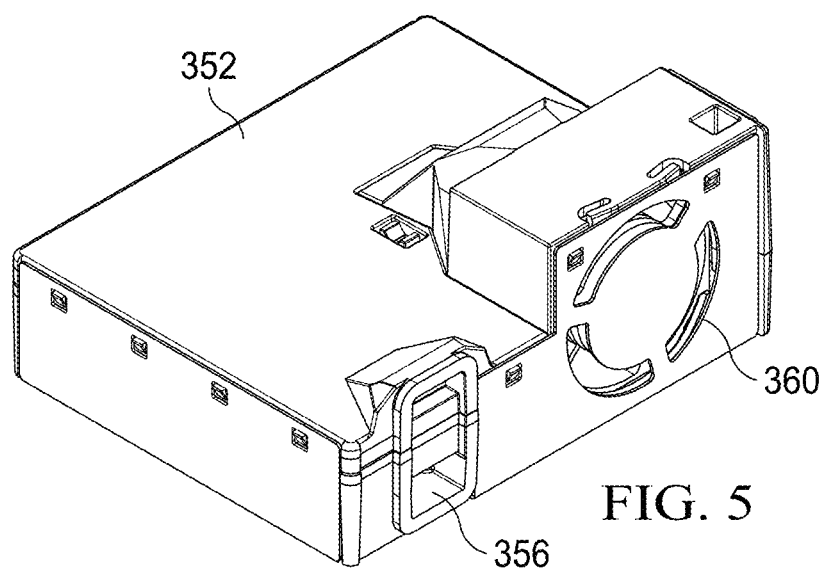
FIG. 5 is a schematic, perspective view of a particulate sensor shown on its side to reveal its sensor intake and sensor outlet according to an illustrative embodiment.

Referring now primarily to FIGS. 3-5, an illustrative embodiment of a first cover 232 is shown. The first cover has a first sidewall 296, a second sidewall 300, a third sidewall 304, a fourth sidewall 308, and a primary wall 312. The first cover 232 has a first concave interior portion 316. A plurality of chamber walls 320 extend from the primary wall 312 of the first cover 232 into the first concave interior portion 316. A perimeter 324 of the first covered 232 may be formed with a lip or ledge 328 to assist with sealing with the second cover 236.

One wall of the plurality of chamber walls 320 is a longitudinal partitioning wall 332 that extends from the primary wall 312 into the first concave interior portion 316. The longitudinal partitioning wall 332 includes a first surface 336 and a second surface 340. The longitudinal partitioning wall 332 has a first aperture 344 (FIG. 4) and a second aperture 348 (FIG. 4). A light pipe or light tube 346 may be included to help direct light produced by aspects of the electronics on the PCB 456, 464 to the first cover 232 where the light is visible through the cover 232.

A particulate sensor 352 disposed on the first surface 336 of the longitudinal partitioning wall 332 with a sensor intake 356 (FIG. 5 in which the sensor 352 is on its side) aligned with the first aperture 344 through the longitudinal partitioning wall 332 and a sensor outlet 360 (FIG. 5) aligned with the second aperture 348 through the longitudinal partitioning wall 332. In one embodiment, the particulate sensor 352 includes a fan that discharges air through the sensor outlet 360. A first particulate-sensor-positioning internal wall 353 and a second particulate-sensor-positioning internal wall 354 may extend from the primary wall to help secure the particulate sensor 352 in position. Wedge members 355 may be included that slope so as to push the sensor downward (for orientation shown) the more the sensor 352 is pushed toward the primary wall 312. That action pushes the sensor 352 onto a gasket 357, which seals the sensor 352 against the surface of the longitudinal partitioning wall.

The longitudinal partitioning wall 332 has a first angled portion 364 that slants downward on an upstream portion 368 and a second angled portion 372 that slants downward on a downstream portion 376 to facilitate removal of any condensate. An intermediate portion 380 that is substantially horizontal or flat when the fourth wall 308 is orthogonal to a gravity field is between the angled portions. The angled portions 364, 372 may angle downward 0.1 to 10 degrees from a horizontal reference. The first cover 232 has a first vent slot 384 (FIG. 2) formed proximate an upstream edge 388 of the longitudinal partitioning wall 332 and a second vent slot 392 (FIG. 6) formed proximate a downstream edge 396 of the longitudinal partitioning wall 332. The "downward," "upward," and "horizontal" are referenced for the orientation when the fourth wall 308 of the first cover 232 is orthogonal to gravity.

The plurality of walls 320 includes an intake chamber wall 400, an intake-low-flow wall 404, an outlet-low-flow wall 408, and an outlet wall 412 that extend outward from the interior side of the main wall 312 of the first cover 232. The referenced walls 400, 404, 408, 412 together with the main wall 312 and a main wall 416 (FIGS. 6 and 8) of the second cover 236 forms at least three chambers: an intake chamber 420, a low-flow chamber 424, and an outlet chamber 428 (shown without the second cover 236 in FIG. 3). The intake-low-flow wall 404 and the outlet-low-flow wall 408 of the plurality of chamber walls 320 that form sidewalls of the low-flow chamber 424 have a vertical portion and an inward angled portion (for orientation of FIG. 3). A cutout or aperture 432 is formed in the inlet-low-flow wall 404, which provides fluid coupling between the intake chamber 420 and the low-flow chamber 424. The cutout 432 is formed on the angled portion of the intake-low-flow wall 404.

Figure 6:
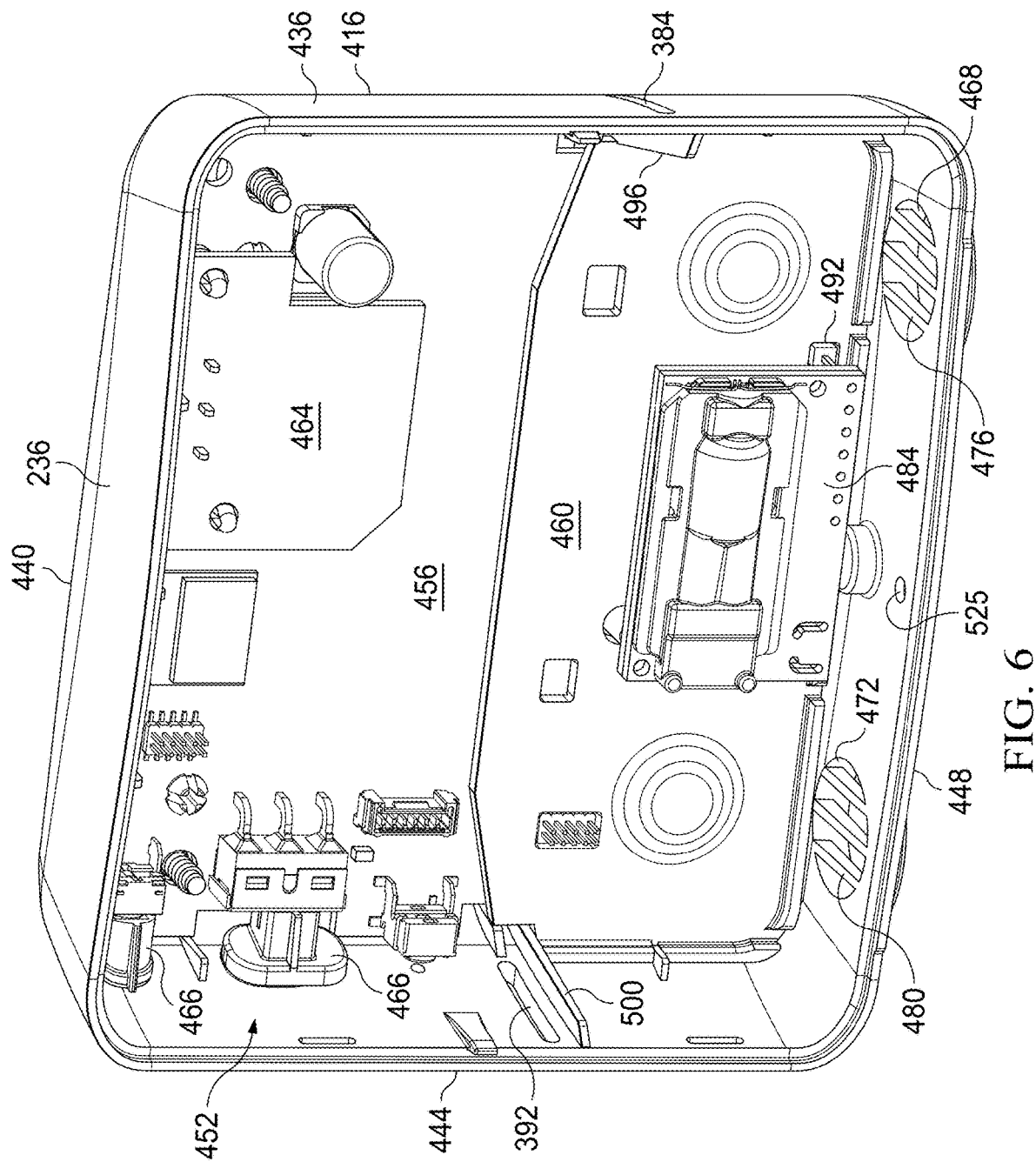
FIG. 6 is a schematic, perspective view of a second cover of an illustrative embodiment of an indoor air quality monitor.
Figure 7:
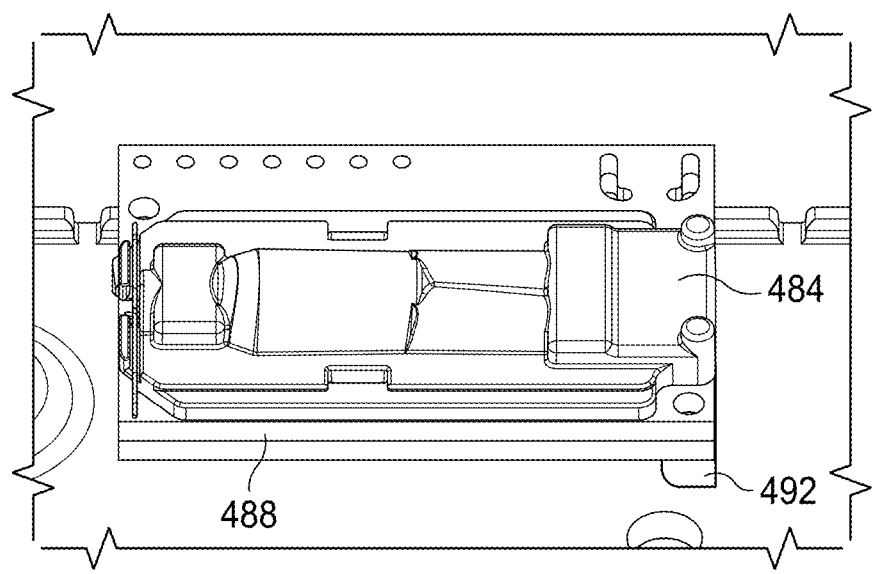
FIG. 7 is a schematic, perspective view from a lower end (for orientation of FIG. 6) of a $CO_2$ sensor according to an illustrative embodiment.

Referring now primarily to FIGS. 6 and 7, an illustrative embodiment of the second cover 236 is presented. The second cover includes a first sidewall 436, a second sidewall 440, the primary wall 416, a third sidewall 444, and a fourth sidewall 448. The second cover 236 has a second concave interior portion 452. An interior surface of the primary 416 may have one or more printed circuit boards (PCB) 456 and at least one wall gasket 460 on a portion. The wall gasket 460 may formed from any suitable material that is non-contaminating, low-offgassing, low VOC, e.g., VITON. A second printed circuit board 464, or daughter board, is shown in front of the other 456. The daughter board 464 may allow for easier switches in production of different connectors. Various components are shown on the PCBs 456, 464 as those skilled in the art will appreciate. The PCB may be secured with ratcheting T's or retainer clips or other fasteners. The electronics on the PCB may include a wireless communications system, e.g., low-energy Bluetooth, that communicates air quality data to other devices as suggested in connection with FIG. 1. Some embodiments include one or more sensor control members 466 that extend through the third wall 444 and are accessible by a user from the exterior. The control members 466 may include switches to deactivate a fan in the particulate sensor, a factor reset button, wireless pairing, power, sensor calibration, etc.

The first cover 232 and second cover 236 mate and couple with the first concave interior portion 316 and the second concave interior portion 452 facing each other and forming an interior cavity when in an assembled position. When assembled, the plurality of chamber walls 320 interfaces at least partially with the wall gasket 460 and form at least the three chambers: the intake chamber 420, the low-flow chamber 424, and the outlet chamber 428. In this embodiment, the fourth sidewall 448 of the second cover 236 is formed with a first aperture 468 and a second aperture 472 for providing fluid access to the intake chamber 420 and outlet chamber 428, respectively. The first aperture 468 may be covered by a first grill 476, and the second aperture 472 may be covered by a second grill 480.

At least one air quality sensor 484, e.g., a $CO_2$ sensor, may be coupled to the inside of the primary wall 416 of the second cover 236 and is sized and configured to be disposed within the low-flow chamber 424 when the indoor air quality monitor 212 is assembled. In one embodiment, a Sensirion SCD30 was used. In one embodiment, the at least one air quality sensor 484 was mounted on a PCB 488 suspended above the gasket 460 or PCB 456 using a post 492.

As seen well in FIG. 6, a first slide rail may be formed on an inside the first wall and a second slide rail formed on an inside of the third wall. In assembling the indoor air quality monitor 212, the slide rails 496, 500 receive the upstream edge 388 and downstream edge 396, respectively, of the longitudinal partitioning wall 332 of the first cover 232. The longitudinal partitioning wall 332 divides the interior cavity into an upper cavity and a lower cavity.

Figure 8:
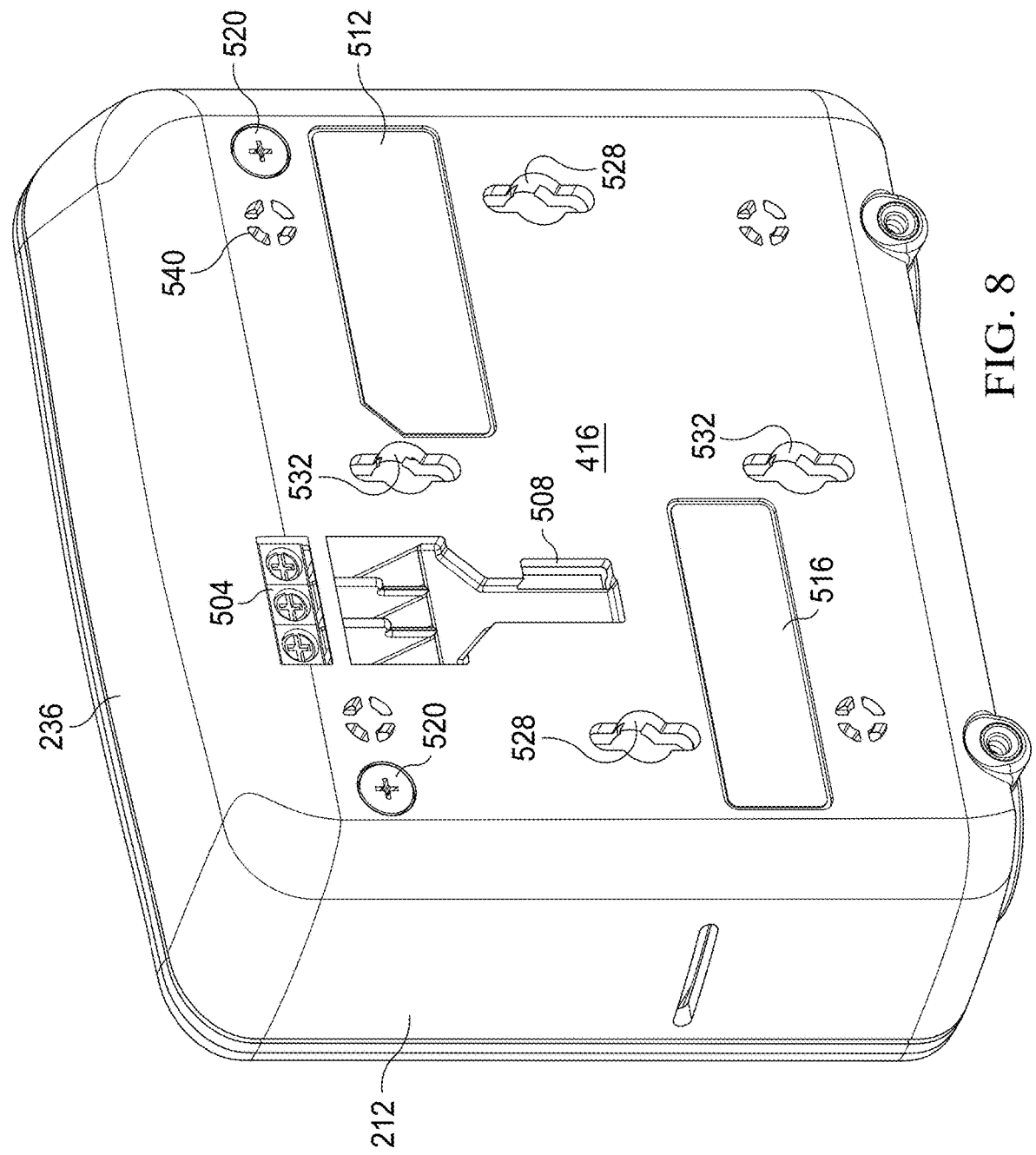
FIG. 8 is a schematic, rear perspective view of a second cover of an illustrative embodiment of an indoor air quality monitor.

Referring now primarily to FIG. 8, an exterior, rear portion of the indoor air quality monitor 212 is presented. The exterior of the primary wall 416 has a three-wire terminal 504. The slot there gives access to screw heads to tighten the clamping mechanism that holds wires in place. An access slot 508 allows access to pins on the PCB 456 or 464 for a final functioning test (FFT). Labeling areas 512, 516 are included for various labels, e.g., FCC information.

A plurality of fasteners 520, e.g., screws, bolts, latches, are included that interface on the other side with fastener bosses 524 (FIG. 3) to help coupled the two covers 232, 236. In addition to the fasteners 520 shown, one or more fasteners may be used such as one on the bottom or fourth wall coming into the monitor 212. In this regard, the screw boss 522 (FIG. 3) may be formed on the fourth wall of the first cover in the low-flow chamber 424 for receiving the fastener 294 (FIG. 2), e.g., screw, bolt, latch, etc. The fastener 294 may go through a fastener aperture 525 (FIG. 6) through the fourth wall of the second cover. In addition, locking members 526 (FIG. 3) may be used to snap into place with the second cover.

A first plurality of keyways 528 and a second plurality of keyways 532 may be included. The mounting bracket 224 (FIG. 2) has mounting posts 244 that interact with the second plurality of keyways 532. The other keyways 528 may be used for direct mounting of the indoor air quality monitor 212 without the bypass chamber 320. Vents 540 are also included. In some embodiments, cutouts 540 may be used make the PCB snap/trees.

Figure 9:
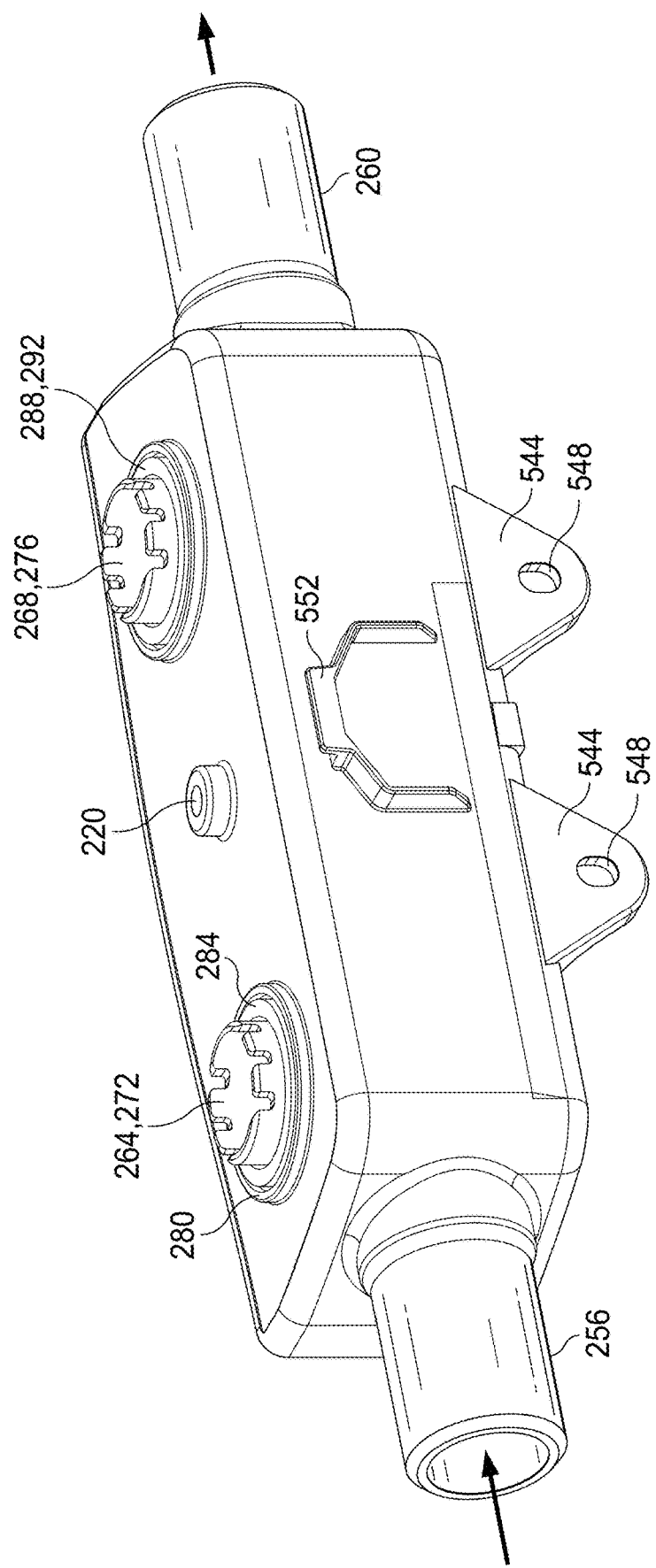
FIG. 9 is a schematic, rear perspective view of a bypass chamber of an illustrative embodiment of an indoor air quality monitor.

Referring now primarily to FIG. 9, a rear side of the bypass chamber 220 is presented. Most aspects of the bypass chamber 220 are described above in connection with FIG. 2. In this view, one may see fastener tabs 544 with fastener apertures 548. Fasteners go through the fastener apertures 548 and into apertures 252 (FIG. 2), or screw bosses, when attaching the bypass chamber 220 to the mounting bracket 224. A mounting hood or shelf 552 is formed on the exterior that interfaces with shelf 248 (FIG. 2) when attaching the bypass chamber 220 to the mounting bracket 224.

The bypass chamber 220 has the intake conduit 256 and an outlet conduit 260. Hose or conduit, e.g., hose 556 (FIG. 1) may be attached to the intake conduit 256 and another hose or conduit 560 may be attached to the outlet conduit 260 when being used to evaluate air from a duct. The bypass chamber 220 has the tributary outlet 264 and a tributary inlet 268. When assembled with the bypass chamber 220, the indoor air quality monitor 212 is arranged so that the tributary outlet 264 is fluidly coupled to the intake chamber 420 and the tributary inlet 268 is fluidly coupled to the outlet chamber 428.

Referring again primarily to FIG. 3-6, in one illustrative embodiment the longitudinal (right and left in FIG. 3) dimension at the fourth wall 308 and going from the 296 to the start of the inlet wall 400 is approximately ¼ inch. The longitudinal dimension at the fourth wall 308 from the inlet wall 400 to the inlet-low-flow wall 440 is ⅝ inch; from the inlet-low-flow wall 440 to the outlet-low-flow wall 408 is 1⅛ inches; from the outlet-low-flow wall 408 to the outlet wall 412 is ¾ inches; and from the outlet wall 412 to the third wall 304 is ¼ inch.

In one embodiment, the longitudinal distance at the fourth wall 308 from the first wall to the third wall is a dimension L and the following longitudinal dimensions apply: from the first wall 296 to the inlet wall 400 is in the range of 0.05 to 0.15 L; from the inlet wall 400 to the inlet-low-flow wall 404 is in the range 0.15 to 0.25 L; from the inlet-low-flow wall 440 to the outlet-low-flow wall 408 is in the range 0.35 to 0.45 L; form the outlet-low-flow wall 408 to the outlet wall 412 is in the range of 0.2 to 0.3 L; and from the outlet wall 412 to the third wall 304 is in the range 0.05 to 0.15 L.

In one illustrative embodiment, the volume ($V_1$) of the intake chamber 420 is less than the volume ($V_2$) of the outlet chamber 428, i.e., $V_1 < V_2$. The first aperture 344, second aperture 348, the tributary inlet 268, tributary outlet 264, and cutout 432 are sized and configured to accommodate the desired fluid flowrates—neither overwhelming nor underwhelming the sensors 352, 484. The cutout 432 in the inlet-low-flow wall 404 is formed on the angled portion with the cutout 432 comprising between 20% and 45% of an area of the inlet-low-flow wall 404.

According to an illustrative embodiment, an indoor air quality monitor as described above further includes a mounting a bracket having a bracket cutout and a bracket shelf, and wherein a back portion of the bypass chamber is formed with a bypass shelf sized and configured to mate with the bracket cutout, wherein a back exterior portion of the bypass chamber comprises a shelf portion that is sized and configured to have portion on the bracket shelf when the bypass chamber and sensor body are mated.

According to an illustrative embodiment, a HVAC system 10 includes a blower 160, a control unit 196 or 192 communicatively coupled to the blower 160 for controlling operation of the blower 160; and an indoor air quality monitor 204, 208 communicatively coupled to the control unit 192 or 196 for providing air quality data thereto. The controller 192, 196 is responsive in activating or deactivating the blower 160 (or an outdoor air dampener or both) in response to the air quality data. The indoor air quality monitor 204, 208 is of the type described above. This may allow the system to not over drive the HVAC system because the air quality is known and is part of a feedback loop. If the air quality is good, the system may remain off if the other parameters, e.g., temperature are acceptable. On the other hand, if the air quality drops below a threshold, the HVAC system's equipment may be activated to improve the air quality. This may be done opening a damper to include outside air or at least activating the blower to filter air.

According to an illustrative embodiment, a method of monitoring air quality in an HVAC system 100 includes fluidly coupling an offtake conduit 556 to a duct 144 of the HVAC system and to an inlet conduit 256 of a bypass chamber 220 of an indoor air quality of monitor 212; fluidly coupling a return conduit 560 to the duct 144 and to an outlet conduit 260 of the bypass chamber 220; coupling the bypass chamber 220 to a monitor body 228 of an indoor air quality monitor 212; siphoning air from the bypass chamber 220 into an interior of the monitor body 228 of the indoor air quality monitor 212, which comprises a particulate sensor 352 and a $CO_2$ sensor 484, wherein the $CO_2$ sensor 484 is in a low-flow chamber 424 in the interior of the monitor body 228 and the particulate sensor 352 pulls air from an intake chamber 420 and discharges the air to an outlet chamber 428; returning air from the outlet chamber 428 to the bypass chamber 320; and returning air through the return conduit 560 from the bypass chamber 320 to the duct 144.

In some embodiments, a TVOC (Total Volatile Organic Compounds) sensor may be included. In one embodiment, TVOC may be located in the cutout in the wall gasket 460 (FIG. 6) to the upper left of the $CO_2$ sensor. The TVOC sensor may be located on the output side of the particle sensor as to not impact the PM sensor readings.

In some embodiments, a veneer or additional surface may be added to the exterior of the first cover 232. It may be ultrasonically welded thereto or otherwise attached.

References to directions herein are with the fourth wall orthogonal to gravity, but it should be understood that the indoor air quality monitor 212 may be used in other orientations.

Although the present invention and its advantages have been disclosed in the context of certain illustrative, non-limiting embodiments, it should be understood that various changes, substitutions, permutations, and alterations can be made without departing from the scope of the invention as defined by the claims. It will be appreciated that any feature that is described in a connection to any one embodiment may also be applicable to any other embodiment.

What is claimed:

1. An indoor air quality monitor for a heating, ventilating, and air conditioning system comprising:
   a first cover having a first sidewall, a second sidewall, a primary wall, a third sidewall, and a fourth sidewall, wherein the first cover has a first concave interior portion;
   a plurality of chamber walls extending from the primary wall of the first cover into the first concave interior portion;
   wherein one of the chamber walls of the plurality of chamber walls comprises a longitudinal partitioning wall extending from the primary wall into the first concave interior portion, the longitudinal partitioning wall having a first surface and a second surface, wherein the longitudinal partitioning wall has a first aperture and a second aperture;
   a particulate sensor disposed on the first surface of the longitudinal partitioning wall with a sensor intake aligned with the first aperture through the longitudinal partitioning wall and a sensor outlet aligned with the second aperture through the longitudinal partitioning wall;
   a second cover having a first sidewall, a second sidewall, a primary wall, a third sidewall, and a fourth sidewall, wherein the second cover has a second concave interior portion;
   wherein the first cover and second cover mate and couple with the first concave interior portion and the second concave interior portion facing each other and forming an interior cavity when in an assembled position;
   a wall gasket disposed on a portion of the second cover in the second concave interior portion;
   wherein, when assembled, the plurality of chamber walls interfaces at least partially with the wall gasket and form at least three chambers: an intake chamber, a low-flow chamber, and an outlet chamber, and wherein the first aperture of the longitudinal partitioning wall is fluidly coupled to the intake chamber and the second aperture of the longitudinal partitioning wall is fluidly coupled to a portion of the outlet chamber, and wherein at least one of the plurality of chamber walls that forms the intake chamber includes a cutout to fluidly couple the intake chamber and the low-flow chamber;
   wherein the fourth sidewall of the second cover is formed with a first aperture and a second aperture for providing fluid access to the intake chamber and outlet chamber, respectively;
   a bypass chamber having an intake conduit and an outlet conduit and having a tributary outlet and a tributary inlet, wherein, when assembled, the tributary outlet is fluidly coupled to the intake chamber and the tributary inlet is fluidly coupled to the outlet chamber; and
   at least one air quality sensor disposed in the low-flow chamber.

2. The indoor air quality monitor of claim 1, wherein the at least one air quality sensor is a $CO_2$ sensor.

3. The indoor air quality monitor of claim 1, wherein the particulate sensor includes a fan and wherein of the intake chamber has a volume $V_1$ that is less than the volume $V_2$ of the outlet chamber.

4. The indoor air quality monitor of claim 1, wherein the bypass chamber further comprises a first ring extension extending around the tributary outlet and second ring extension extending around the tributary inlet.

5. The indoor air quality monitor of claim 1, wherein the bypass chamber further comprises a first ring extension extending around the tributary outlet and having a first seal groove about the first ring extension, and a second ring extension extending around the tributary inlet and having a second seal groove about the second ring extension; and further comprising a first O-ring disposed in the first seal groove and a second O-ring disposed in the second seal groove.

6. The indoor air quality monitor of claim 1, wherein the longitudinal partitioning wall has a first angled portion that slants downward on an upstream portion and a second angled portion that slants downward on a downstream portion to facilitate removal of any condensate and wherein the first cover has a first vent slot formed proximate an upstream edge of the longitudinal partitioning wall and a second vent slot formed proximate a downstream edge of the longitudinal partitioning wall, wherein downward and upward are referenced for the orientation when the fourth wall of the first cover is orthogonal to gravity.

7. The indoor air quality monitor of claim 1, wherein a intake-low-flow wall and a outlet-low-flow wall of the plurality of chamber walls that form sidewalls of the low-flow chamber have a vertical portion and an inward angled portion, wherein the cutout in the outlet-low-flow wall with the intake chamber is formed on the angled portion, and wherein vertical is referenced for the orientation when the fourth wall of the first cover is orthogonal to gravity.

8. The indoor air quality monitor of claim 1, wherein a first slide rail is formed on the first sidewall of the second cover and a second slide rail is formed on the third sidewall of the second cover within the second concave interior portion for receiving at least a portion of the longitudinal partitioning wall of the first cover when in the assembled position such that the interior cavity is at least partially partitioned to form an upper cavity and a lower cavity.

9. The indoor air quality monitor of claim 1, further comprising a first grill formed on the second cover over the first aperture and a second grill formed on the second cover over the second aperture.

10. The indoor air quality monitor of claim 1, wherein the top cover has a longitudinal dimension L, and wherein the intake chamber comprises between 0.2 to 0.35 L, the low-flow chamber comprises between 0.3 to 0.4 L, and an outlet chamber comprises 0.15 to 0.35 L.

11. The indoor air quality monitor of claim 1, wherein a first member and second member of the plurality of chamber walls that form sidewalls of the low-flow chamber have a vertical portion, when the fourth sidewall is orthogonal with a gravity field, and an inward angle portion and wherein the cutout in the wall shared with the intake chamber and the low-flow chamber is formed on the angled portion with the cutout comprising between 20% and 45% of an area of the wall shared with the intake chamber and the low-flow chamber.

12. The indoor air quality monitor of claim 1, wherein the at least one air quality sensor is a $CO_2$ sensor, and wherein the $CO_2$ sensor is suspended within the low-flow chamber.

13. The system of claim 1, further comprising:
wherein the at least one air quality sensor is a $CO_2$ sensor;
wherein the bypass chamber further comprises a first ring protrusion extending around the tributary outlet and having a first seal groove, and a second ring protrusion extending around the tributary inlet and having a second seal groove;
a first O-ring disposed in the first seal groove and a second O-ring disposed in the second seal groove;
wherein the longitudinal partitioning wall has an angle down between 0.1 and 10 degrees on each exterior edge, and wherein the first surface of the longitudinal partitioning wall aligns with a first vent formed on the first sidewall of the second cover and aligns with a second vent formed on the third sidewall of the second cover;
a first slide rail is formed on the first sidewall of the second cover and a second slide rail is formed on the third sidewall of the second cover within the second concave interior portion for receiving at least a portion of the longitudinal partitioning wall of the first cover when in the assembled position such that the interior cavity is at least partially partitioned to form an upper cavity and a lower cavity;
the first cover has a longitudinal dimension L, and wherein the intake chamber comprises between 0.2 to 0.35 L, the low-flow chamber comprises between 0.3 to 0.4 L, and an outlet chamber comprises 0.15 to 0.3 L;
wherein a first member and second member of the plurality of chamber walls that form sidewalls of the low-flow chamber have a vertical portion, when the fourth sidewall is orthogonal to gravity, and has an inward angled portion, and wherein the cutout in the wall shared with the intake chamber and the low-flow chamber is formed on the angled portion with the cutout comprising between 20% and 45% of an area of the wall shared with the intake chamber and the low-flow chamber; and
further comprising a first grill formed on the second cover over the first aperture and a second grill formed on the second cover over the second aperture.

14. An HVAC system comprising:
a blower;
a control unit communicatively coupled to the blower for controlling operation of the blower;
an indoor air quality monitor communicatively coupled to the control unit for providing air quality data thereto;
wherein the controller is responsive in activating or deactivating the blower in response to the air quality data; and
wherein the indoor air quality monitor comprises:
a monitor body having an interior cavity,
a plurality of chambers formed within the interior cavity,
a longitudinal partitioning wall disposed within the interior cavity of the monitor body, the longitudinal partitioning wall having a first surface and a second surface and a first aperture and a second aperture,
wherein one of the plurality of chambers within the interior cavity comprises an intake chamber, and wherein the intake chamber is fluidly coupled to a first aperture in the monitor body,
wherein another of the plurality of chambers within the interior cavity comprises an outlet chamber, wherein the outlet chamber is fluidly coupled to a second aperture in the monitor body,
wherein another of the plurality of chambers within the interior cavity comprises a low-flow chamber that is fluidly coupled to the intake chamber,
a particulate sensor disposed on the first surface of the longitudinal partitioning wall with a sensor intake aligned with the first aperture through the longitudinal partitioning wall and a sensor outlet aligned with the second aperture through the longitudinal partitioning wall and wherein the first sensor intake is fluidly coupled to the intake chamber, wherein the particulate sensor comprises a fan for pulling air from the intake chamber, and
a $CO_2$ sensor fluidly disposed within the low-flow chamber.

15. The HVAC system of claim 14, wherein the monitor body of the indoor air quality monitor comprises a top cover and bottom cover, and wherein the top cover comprises a plurality of walls extending outwardly into an interior cavity that form the plurality of chambers as the plurality of walls interface with a primary wall of the bottom cover.

16. The HVAC system of claim 14, wherein the sensor body of the indoor air quality monitor has a longitudinal length L and wherein the intake chamber has a longitudinal length that is between 20%-30% L, the low-flow chamber has a longitudinal length between 30%-40% L, and the outlet chamber has a longitudinal length between 25% and 35% L.

17. The HVAC system of claim 14, wherein the indoor air quality monitor further comprises a bypass chamber having an intake conduit, an outlet conduit, a tributary outlet, and a tributary inlet, and wherein the tributary outlet is fluidly coupled to the intake chamber, and the tributary inlet is fluidly coupled to the outlet chamber.

18. A method of monitoring air quality in an HVAC system, the method comprising:
- fluidly coupling an offtake conduit to a duct of the HVAC system and to an inlet conduit of a bypass chamber of an indoor air quality monitor;
- fluidly coupling a return conduit to the duct and to an outlet conduit of the bypass chamber;
- coupling the bypass chamber to a monitor body of the indoor air quality monitor;
- siphoning air from the bypass chamber into an interior of the monitor body of the indoor air quality monitor, which comprises a particulate sensor and a $CO_2$ sensor, wherein the $CO_2$ sensor is in a low-flow chamber in the interior of the monitor body, the particulate sensor is mounted on a longitudinal wall disposed within the interior of the monitor body, and the particulate sensor includes a fan that pulls air from an intake chamber and discharges the air to an outlet chamber;
- wherein, a sensor inlet of the particulate sensor is aligned with a first aperture in the longitudinal wall and a sensor outlet of the particulate sensor is aligned with a second aperture in the longitudinal wall;
- returning air from the outlet chamber to the bypass chamber;
- returning air through the return conduit from the bypass chamber to the duct.

* * * * *